United States Patent
Dietz et al.

(10) Patent No.: US 6,840,954 B2
(45) Date of Patent: Jan. 11, 2005

(54) SYSTEMS AND METHODS USING VASOCONSTRICTION FOR IMPROVED THERMAL TREATMENT OF TISSUES

(75) Inventors: Timothy G. Dietz, Califon, NJ (US); Stanley Levy, Jr., Saratoga, CA (US)

(73) Assignee: Solarant Medical, Inc., Livermore, CA (US)

( * ) Notice: Subject to any disclaimer, the term of this patent is extended or adjusted under 35 U.S.C. 154(b) by 0 days.

(21) Appl. No.: 10/029,000

(22) Filed: Dec. 20, 2001

(65) Prior Publication Data

US 2003/0120326 A1 Jun. 26, 2003

(51) Int. Cl.⁷ .............................. A61F 7/12; A61F 7/00
(52) U.S. Cl. ........................ 607/96; 607/99; 607/104
(58) Field of Search ................ 607/96–105; 606/33–41, 606/42–52

(56) References Cited

U.S. PATENT DOCUMENTS

| | | | |
|---|---|---|---|
| 728,883 | A | 5/1903 | Downes |
| 4,679,561 | A | 7/1987 | Doss |
| 4,765,331 | A | 8/1988 | Petruzzi et al. |
| 5,201,732 | A | 4/1993 | Parins et al. |
| 5,282,799 | A | 2/1994 | Rydell |
| 5,423,811 | A | 6/1995 | Imran et al. |
| 5,458,596 | A | 10/1995 | Lax et al. |
| 5,496,312 | A | 3/1996 | Klicek |
| 5,514,130 | A | 5/1996 | Baker |
| 5,569,242 | A | 10/1996 | Lax et al. |
| 6,139,571 | A | * 10/2000 | Fuller et al. ............... 607/105 |
| 6,162,242 | A | * 12/2000 | Peyman ........................ 607/88 |
| 6,283,987 | B1 | * 9/2001 | Laird et al. .................. 607/96 |
| 6,470,219 | B1 | * 10/2002 | Edwards et al. ............ 607/101 |
| 6,544,248 | B1 | * 4/2003 | Bass .......................... 604/511 |
| 6,562,835 | B1 | * 5/2003 | Caruso ...................... 514/289 |

FOREIGN PATENT DOCUMENTS

WO  WO 00/59393 A1  10/2000

* cited by examiner

Primary Examiner—Roy D. Gibson
(74) Attorney, Agent, or Firm—Townsend and Townsend and Crew LLP; Lynn M. Thompson

(57) ABSTRACT

The present invention enhances the effectiveness of treatment of support tissue structures. Generally, such tissue structures support organs and hold the organs in their proper position for appropriate functioning. When such tissue structures become weak, hyper-elastic, and/or excessively lengthy, the organs of are no longer supported in their proper position. This often leads to physical manifestations such as incontinence, hernias, and the like. Remedies often involve thermal treatment of the support tissue structures, such as thermally inducted controlled shrinkage, contraction, or stiffening of the support tissue structure. To enhance such thermal treatment and diminish the possibility of undesirable heating and damage to nearby tissue surfaces, vasoconstrictive agents are used.

157 Claims, 10 Drawing Sheets

SYSTEMS AND METHODS USING VASOCONSTRICTION FOR IMPROVED THERMAL TREATMENT OF TISSUES

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

1. Field of the Invention

The present invention generally relates to medical devices, methods, and systems. More specifically, the present invention provides techniques for improving the effectiveness of selectively heating tissues, particularly for the noninvasive treatment of urinary incontinence and hernias, for cosmetic surgery, and the like.

Urinary incontinence arises in both women and men with varying degrees of severity, and from different causes. In men, the condition occurs almost exclusively as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external sphincter, and most often, to the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such noninterventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Each of these procedures has associated shortcomings. Surgical operations which involve suturing of the tissue structures supporting the urethra or bladder neck region require great skill and care to achieve the proper level of artificial support. In other words, it is necessary to occlude or support the tissues sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections. Therefore, it would be desirable to provide an improved therapy for urinary incontinence.

A variety of other problems can arise when the support tissues of the body have excessive length. Excessive length of the pelvic support tissues (particularly the ligaments and fascia of the pelvic area) can lead to a variety of ailments including, for example, cystocele, in which a portion of the bladder protrudes into the vagina. Many hernias are the result of a strained, torn, and/or distended containing tissue, which allows some other tissue or organ to protrude beyond its contained position. Cosmetic surgeries are also often performed to decrease the length of support tissues. For example, abdominoplasty (often called a "tummy tuck") is often performed to decrease the circumference of the abdominal wall. The distortion of these support tissues may be due to strain, advanced age, congenital predisposition, or the like.

Unfortunately, many support tissues are difficult to access, and their tough, fibrous nature can complicate their repair. As a result, the therapies now used to improve or enhance the support provided by the ligaments and fascia of the body often involve quite invasive surgical procedures.

For these reasons, it would be desirable to provide improved devices, methods, and systems for treating fascia, tendons, and the other support tissues of the body. It would be particularly desirable to provide improved noninvasive or minimally invasive therapies for these support tissues, especially for the treatment of urinary incontinence in men and women. It would further be beneficial to provide techniques which would improve the effectiveness of heat-treatment, reduce the power required for such treatment and thus minimize collateral damage.

2. Description of the Background Art

U.S. Pat. No. 5,423,811 describes a method for RF ablation using a cooled electrode. U.S. Pat. Nos. 5,458,596 and 5,569,242 describe methods and an apparatus for controlled contraction of soft tissue. An RF apparatus for controlled depth ablation of soft tissue is described in U.S. Pat. No. 5,514,130.

U.S. Pat. No. 4,679,561 describes an implantable apparatus for localized heating of tissue, while U.S. Pat. No. 4,765,331 describes an electrosurgical device with a treatment arc of less than 360 degrees. An impedance and temperature generator control is described in U.S. Pat. No. 5,496,312. Bipolar surgical devices are described in U.S. Pat. Nos. 5,282,799, 5,201,732, and 728,883.

BRIEF SUMMARY OF THE INVENTION

The present invention enhances the effectiveness of treatment of support tissue structures. Generally, such tissue structures support organs and hold the organs in their proper position for appropriate functioning. When such tissue structures become weak, hyper-elastic, and/or excessively lengthy, the organs of are no longer supported in their proper position. This often leads to physical manifestations such as incontinence, hernias, and the like. Remedies often involve thermal treatment of the support tissue structures, such as thermally inducted controlled shrinkage, contraction, or stiffening of the support tissue structure. To enhance such thermal treatment and diminish the possibility of undesirable heating and damage to nearby tissue surfaces, vasoconstrictive agents are used.

Methods of treating a hyperextended support tissue of a patient body by shrinkage or contraction typically comprises electrically coupling a first electrode and a second electrode to the tissue. An electrical potential is applied across the electrodes while controlling the separation distance between the electrodes. As a result of the separation control, an electrical current within the tissue heats and shrinks the tissue to a more desirable length. Tissue contraction results from the heating by affecting the collagen molecules of the tissue, specifically heat-induced uncoiling and repositioning of the collagen β-pleated structure. Typically, the tissue is heated to between about 60° C. and 110° C., often being between about 60° C. and 80° C. This will generally effect a shrinkage of the target tissue in at least one dimension of between 20 to 50 percent. In most situations, heating energy will be applied for a period of from 30 seconds to 5 minutes. These heating times will vary with the type and arrangement of electrodes used. The total amount of energy delivered will depend in part on which tissue structure is being treated, how much tissue is disposed between the target tissue and the heating element, and the specific temperature and time selected for the protocol. The power delivered will often be in the range from 10W to 100W, usually being about 30W. The temperature will usually not drop instantaneously when the heating energy stops, so that the tissue may remain at or near the therapy temperature for a time from about 10 seconds to about 2 minutes, and will often cool gradually back to body temperature.

A variety of devices and methods may be used to provide resistive heating to support tissues. These typically involve the use of a probe comprising a shaft having a proximal end, a distal end, and first and second electrodes disposed near the distal end of the shaft. These electrodes are simultaneously engageable against the tissue or fascia and are separated by a predetermined distance which limits depth of tissue heating. A handle is typically adjacent to the proximal end of the shaft for manipulating the electrodes from outside the patient body. Embodiments of such devices and methods are provided in U.S. Pat. No. 6,091,995 (Attorney Docket No. 017761-000120US) which generally describes laparoscopic and other minimally invasive devices, methods, and systems for shrinking tissues, particularly for treatment of incontinence. Likewise, U.S. Pat. No. 6,156,060 (Attorney Docket No. 017761-000910US) is directed to static devices and methods to shrink tissues for incontinence. These patents are assigned to the present assignee, and their full disclosures are incorporated herein by reference.

In some instances, it is desired to direct electrical energy through an intermediate tissue to a targeted portion of fascia. To avoid thermal injury to the intermediate tissue, cooled plate electrodes are used. Such a cooled plate electrode is capable of directing electrical energy through an intermediate tissue and into fascia while the cooled electrode prevents injury to the intermediate tissue. In some embodiments, a pair of electrodes having large, substantially planar tissue engaging surfaces are aligned substantially parallel to each other with the fascia and adjacent tissues disposed therebetween. The surfaces of the electrodes which engage the tissue are cooled by a cooling system. The cooling system typically includes a conduit through the electrode for the circulation of cooling fluid, but may optionally rely on thermoelectric cooling or the like. Ideally, the cooling system cools an arc which extends beyond the energized electrode surfaces to prevent any hot spots adjacent the tissue surface, and to maximize the heat removal from the tissue without having to resort to freezing the tissue. Embodiments of such devices and methods are provided in U.S. Pat. No. 6,081,749 (Attorney Docket No. 017761-000320US) which generally describes noninvasive devices, methods, and systems for shrinking of tissues, often by cooling a surface of an intermediate tissue and directing energy through the cooled intermediate tissue to the target tissue so as to effect shrinkage. This patent is assigned to the present assignee, and its full disclosure is incorporated herein by reference.

Methods of treating a weak or overly elastic support tissue of a patient body may be achieved by stiffening the tissue or increasing its modulus of elasticity. The increase in modulus can be affected by directing sufficient energy into the facial tissue so as to promote the formation of scar tissue. The resulting scar tissue is generally significantly less elastic than the original fascia, and may also have an increased thickness either as a result of facial shrinkage or from the proliferation of scar tissue and/or smooth muscle cells. This local increase in modulus of the scarred support tissue can transfer stress and strain from the area of treatment to adjoining areas, and may also shortened the response time of the tissue plane to stress pulses such as those which might result in incontinence events. Such scarring will preferably be promoted by directing energy into the fascial tissue so as to injure the fascial tissue without ablating the fascial tissue. While such energy can be delivered in the form of ultrasound, microwave, laser or thermal conduction, it will preferably be in the form of an arc of current conducted through the tissue so that the tissue's impedance effects heating. Heating the fascial tissue to a temperature about 45° C. or more is sufficient to promote the formation of scar tissue and thereby decrease elasticity. Hence, elasticity can be reduced by heating the tissue below the temperatures generally used to effect contraction or shrinkage (typically over about 60° C.). These lower tissue temperatures can significantly reduce collateral damage, particular where the elasticity of the tissue is reduced without significant shrinkage. Embodiments of such devices and methods are provided in U.S. Pat. No. 6,292,700 (Attorney Docket No. 017761-001810US) which is assigned to the present assignee, and its full disclosure is incorporated herein by reference.

As elasticity reduction and shrinking represent two distinct structural alterations to the tissue system, they may be applied independently or in selective combinations so as to provide the desired change in structural support. In any case, although the above described devices and methods have been designed to minimize collateral damage imposed on the treated and adjacent tissues during therapy, additional safeguards and improvements in therapy are desired. Whether heating tissue to 45° C., for elasticity reduction, or 60° C. or above, for shrinking, attempting to heat tissue above normal body temperature (37° C.) will be blunted by the natural heat sinking effect of the cooler blood flow (flowing at body temperature) through the target region. In addition, a vasodilation effect will naturally occur increasing the flow volume and tissue contact area of the blood in the region being heated. Thus, an unwanted cooling mechanism will be attempting to counter the desired therapeutic heating effect.

The present invention provides methods and systems for counteracting these natural cooling effects with the use of vasoconstricting agents. Vasoconstricting agents cause the smooth muscle cells of arteries to contract and decrease the vessel radius. This diminishes the flow volume and tissue contact area of the blood in the region being heated thus decreasing the effectiveness of blood flow as a heat sink. This allows the target tissue to be heated to the desired therapeutic effect with less power applied. This in turn reduces the need to increase energy from the probe which may cause undesirable heating and damage to intervening surface tissue.

Other objects and advantages of the present invention will become apparent from the detailed description to follow, together with the accompanying drawings.

DETAILED DESCRIPTION OF THE INVENTION

While the description is generally directed at devices and methods for treatment of urinary stress incontinence of a female patient, it will be appreciated that the present invention will find many other applications for utilizing vasoconstrictive agents while selectively directing therapeutic heating energy into the tissues of a patient body for shrinking of tissues, for ablation of tissues and tumors, and the like. For example, additional conditions which may be treated include cystocele (a posterior portion of the bladder protrudes into the vagina), enterocele (a hernial protrusion through a defect in the rectovaginal or vesicovaginal pouch), rectocele (prolapse or herniation of the rectum), uterovaginal prolapse (downward movement of the uterus so that the cervix extends into or beyond the vaginal orifice), hernia (portion of the stomach protrudes through an enlarged esophageal hiatus of the diaphragm), or inguinal or abdominal hernia (portion of the small intestine protrudes through the inguinal canal), to name a few.

For Use in Bladder Support

Figure 1:
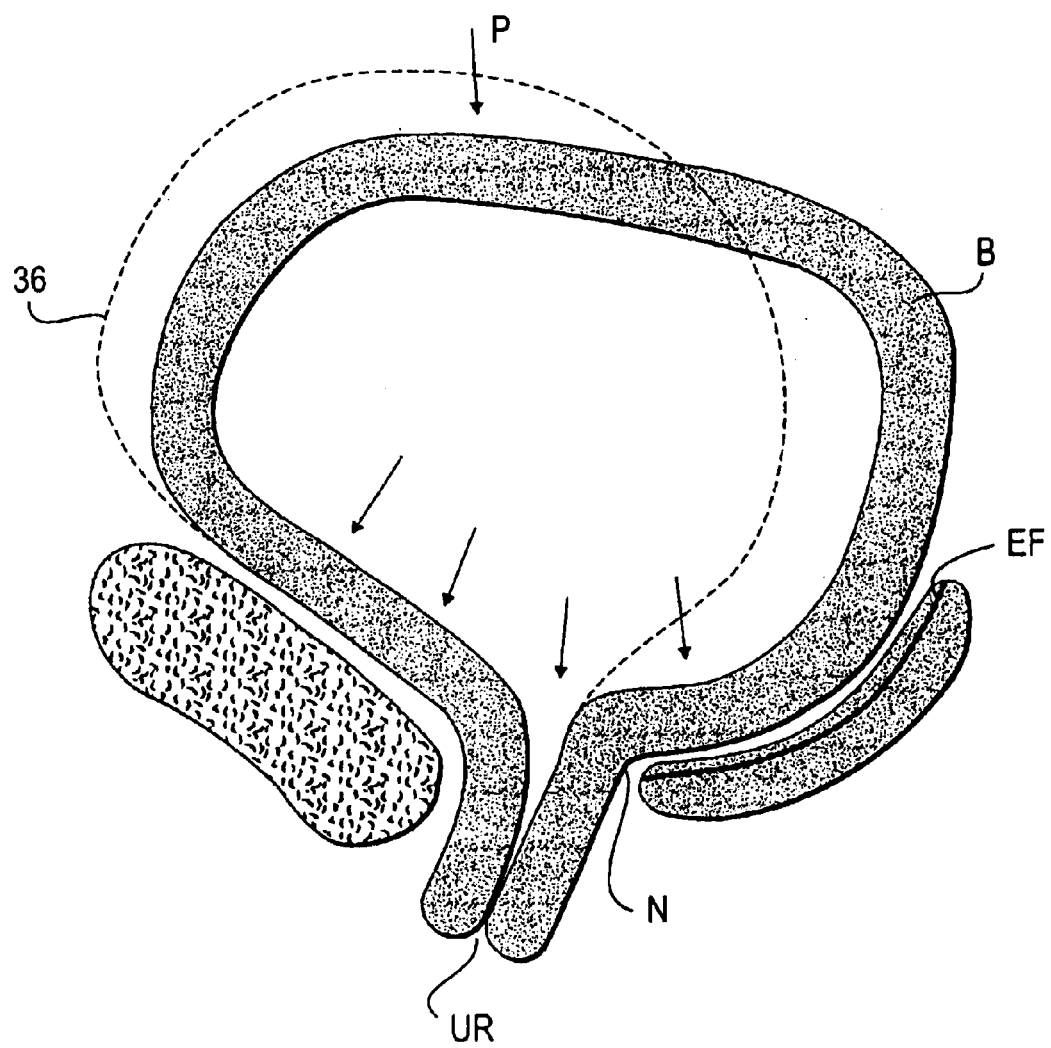
FIG. 1 illustrates the bladder of a urinary stress incontinent patient wherein the bladder has dropped from its nominal position.

Pelvic support tissues generally maintain the position of the urinary bladder B in its proper position. Of particular importance for the methods of the present invention, the endopelvic fascia EF is one of the pelvic support tissues which helps to maintain such position. The endopelvic fascia EF defines a hammock-like structure which largely defines the pelvic floor. In women with urinary stress incontinence due to bladder neck hypermobility, the bladder has typically dropped between about 1.0 and 1.5 cm or more below its nominal position. This condition is typically due to weakening of the pelvic support structures, including the endopelvic fascia and the surrounding ligaments and muscles. Referring to FIG. 1, the bladder B can be seen to have dropped from it's nominal position (shown in phantom by outline 36). While endopelvic fascia EF still supports bladder B to maintain continence when the patient is at rest, a momentary pulse P opens the bladder neck N resulting in a release through urethra UR. Such a pulse P may result from sneezing, coughing, laughing or exercising wherein the abdominal pressure increases momentarily.

The present invention provides a therapy which enhances the effectiveness of heat treatments which apply heating to shrink the length of a target tissue or support tissue and return the bladder B to its nominal position. In this example, the target tissue is the endopelvic fascia EF to which heat is applied to effect such shrinkage and repositioning.

Figure 2:
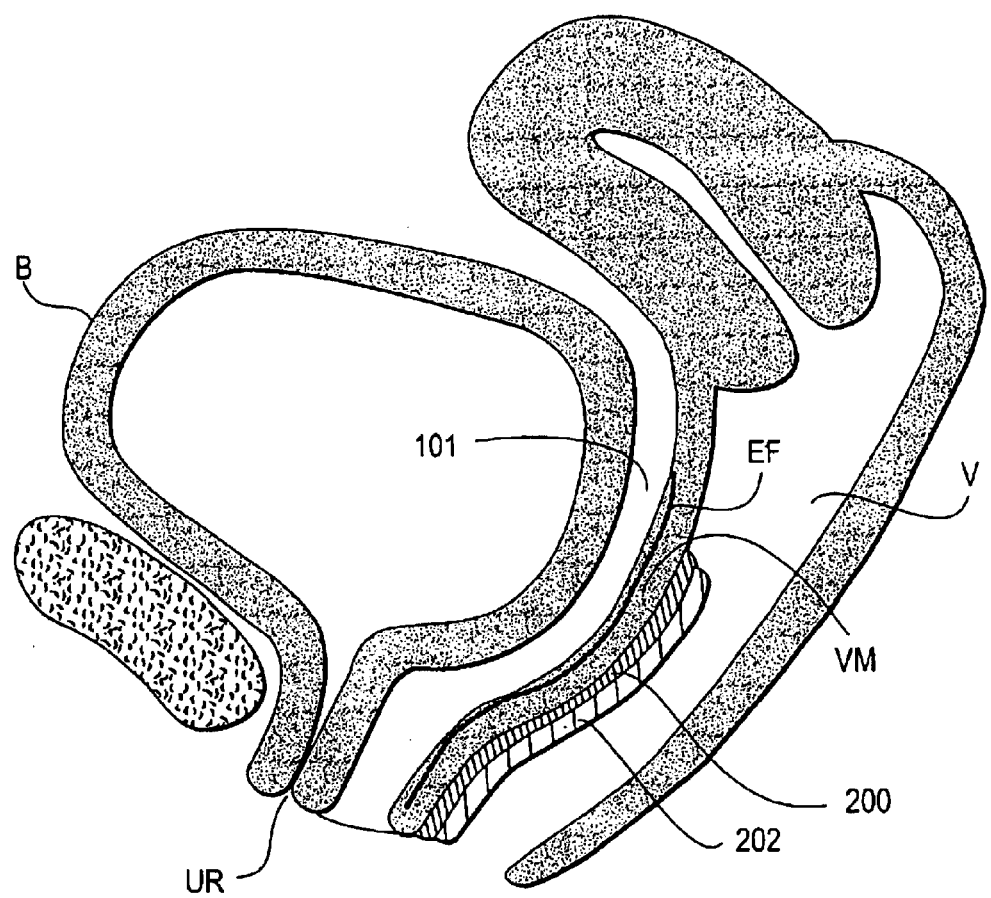
FIG. 2 illustrates a method step of inserting a vasoconstrictive agent into the vagina of a patient.

Typically, the patient is admitted to an ambulatory surgery setting 1–2 hours before surgery. At this time, as shown in FIG. 2, a vasoconstrictive agent 200 is inserted into the vagina V and applied to the vaginal mucosa VM on the anterior vaginal wall medially at the urethra UR and extending laterally from both sides of the urethra UR. One possible agent comprises epinephrine. This is typically provided in a solution comprising water, saline or other liquid, optionally also containing an anesthetic agent, such as lidocaine, or any other additional additive. The solution typically has a concentration of 1 mg agent (such as epinephrine) per 50 ml solution but may range from approximately 1 mg agent per 25 ml solution to 1 mg agent per 200 ml solution. It may be appreciated that any suitable vasoconstrictive agent may be used in any concentration. Likewise, the agent may be provided in forms other than in solution, such as in a paste or other form. The agent 200 may is then applied to a carrier 202, such as a gauze pad, which is held against the anterior wall.

Figure 3:
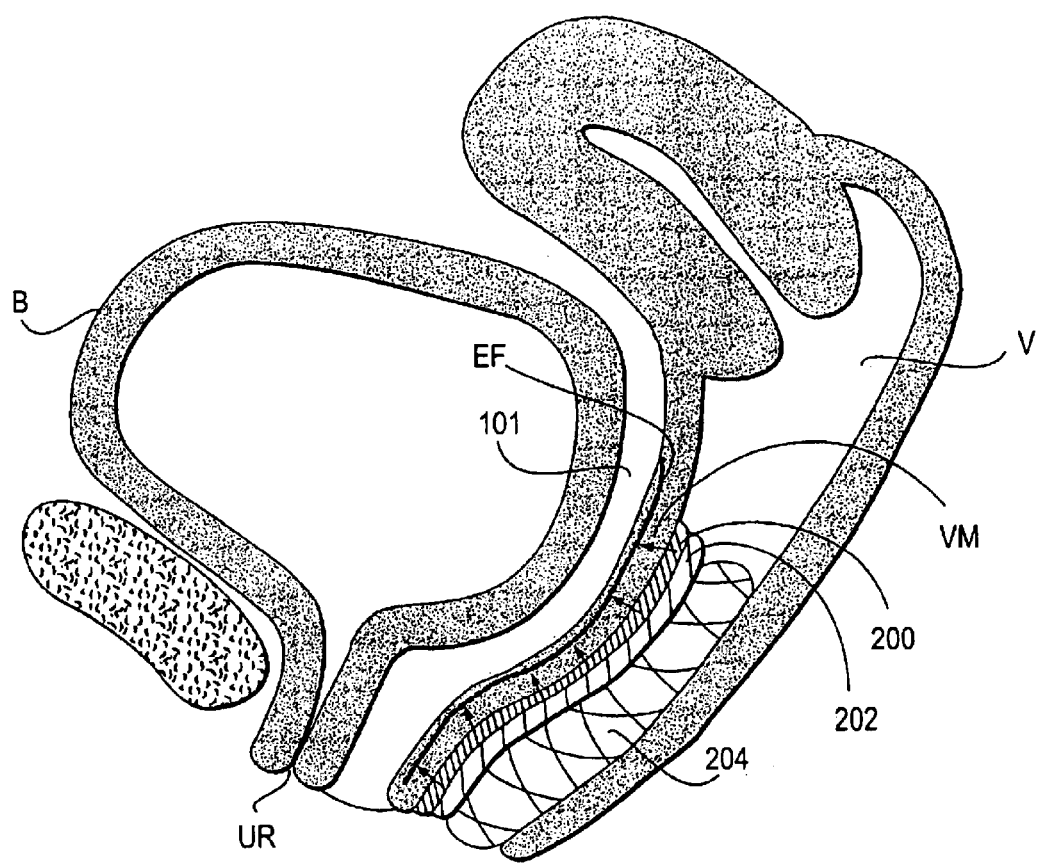
FIG. 3 illustrates the period of absorption of the vasoconstrictive agent.

As shown in FIG. 3, the agent 200 and carrier 202 may be held in place by packing the vagina V with additional material 204, such as additional gauze. The agent 200 is left in place for a period of time to allow absorption of the agent 200 through the vaginal surface tissues and into the vaginal mucosa VM, as illustrated by arrows, to a desired depth of approximately 10–15 mm. The time required for such absorption is typically 30–40 minutes but may range from 15 minutes to 1 hour.

Absorption may be assisted by a variety of methods. For example, when an ionized vasoconstrictive agent 200 is used, the ionized vasoconstrictive agent 200 and target tissue may be electrically stimulated. This causes the vasoconstrictive agent 200 to be absorbed by iontophoresis. Alternatively, ultrasonic stimulation may assist the absorption of vasoconstrictive agent 200 into the target tissue. Or, the vasoconstrictive agent 200 may be injected directly into the target tissue using a needle/syringe system. Thus, it may be appreciated that one or more vasoconstrictive agents may be delivered and/or absorbed into the vaginal mucosa VM or target tissue by a variety of methods other than by the methods illustrated in FIGS. 2–3. During and after absorption, the target tissue forms a vasoconstricted target tissue and will be denoted by shading.

To effect shrinkage of the endopelvic fascia EF, a variety of devices and methods may be used to apply resistive heating to the endopelvic fascia EF. In these exemplary embodiments, the heating energy will typically be applied using an electrode capable of delivering radiofrequency (RF) energy directly against the supporting tissues in a monopolar or bipolar manner. One or more electrodes are typically disposed on one or more probes. Such probes will be substantially rigid and appropriately sized and shaped to be positionable so that the electrodes are placed near the target tissue. For insertion into the vagina, the probe may be sized and shaped to have a length between approximately 4 cm and 8 cm and have a width or diameter between approximately 1.5 cm and 3.0 cm. The probes may be composed of a plastic (such as polyester, polycarbonate, or the like) or an inert metal (such as gold plated brass, or the like), or other biocompatible materials that are typical of intravaginal devices.

The electrodes can take a variety forms, including curved electrodes. It should be appreciated that any number of electrodes and a variety of shaped electrodes can be used. A description of various types of electrodes that can be used with the devices and methods of the present invention are shown and described in commonly assigned U.S. Pat. No. 6,091,995, the complete disclosure of which is incorporated herein by reference. Further, a power supply may be used that is in electrical communication with the electrode assembly though electrical couplings. Optionally, a controller may be incorporated into the probe or the power supply to control the delivery of energy to the heating electrodes. Some exemplary controllers are described in commonly assigned U.S. Pat. No. 6,081,749, the complete disclosure of which is incorporated herein by reference.

In addition to RF energy, the devices, systems and methods of the present invention can rely on other energy sources, such as microwave, light (laser) energy, electrical resistance heating, the delivery of heated fluids, the focusing of ultrasound energy, or any other known energy delivery technique which can be targeted to specific tissue and raise the tissue temperature to the desired range.

Figure 4:
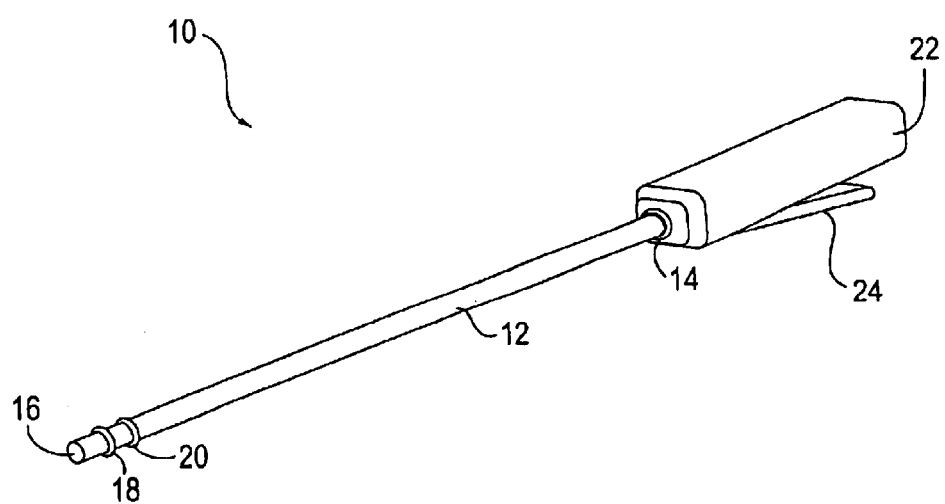
FIG. 4 is a perspective view of a tissue contraction probe which may be used in conjunction with the methods of the present invention.

In preferred embodiments, tissue contraction is achieved by delivery of energy from a single probe. Referring to FIG. 4, an embodiment of a tissue contraction probe 10 used to deliver RF energy is shown to include a shaft 12 having a proximal end 14 and a distal end 16. First and second electrodes 18, 20 are disposed near distal end 16 of shaft 12, while handle 22 is disposed at the proximal end of the shaft. A switch 24 applies a radiofrequency electrical potential across first and second electrodes 18, 20 to effect gentle resistive heating of electrically conductive tissues which span these electrodes. In some embodiments, tissue heating temperatures will be measured directly using a temperature sensor mounted on the probe between the first and second electrodes 18, 20, or separately inserted into the tissue via an ultrasonically or fluoroscopically guided temperature probe. Alternatively, tissue temperature, contraction and the like may be determined indirectly by monitoring the electrical characteristics of the tissue itself.

Figure 5:
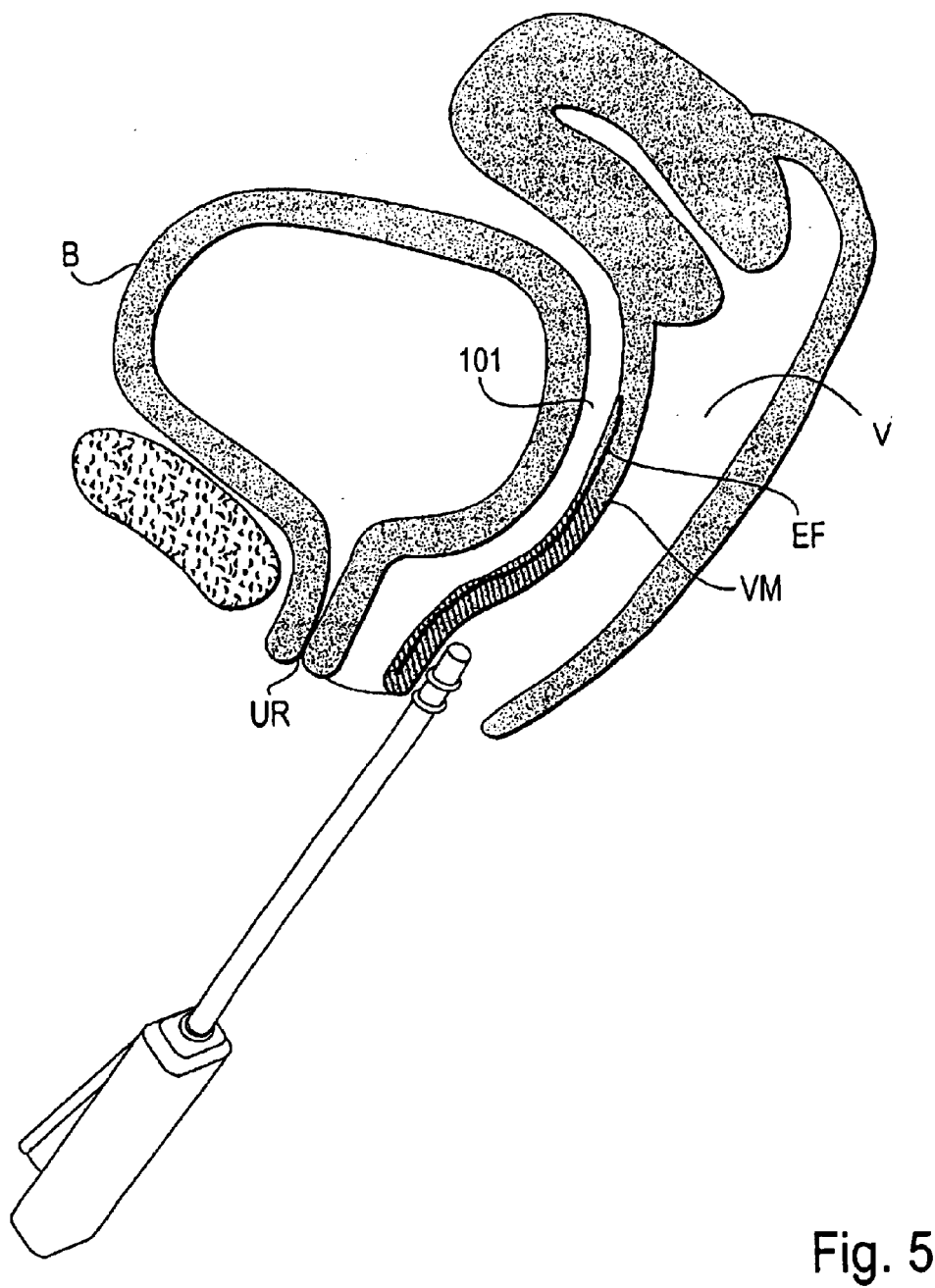
FIG. 5 illustrates the probe of FIG. 4 positioned within the vagina to treat the target tissue.

Referring to FIG. 5, the probe 10 and vagina V are lubricated with electroconductive gel and the probe 10 is introduced to the vagina V. The probe 10 is positioned to treat the vasoconstricted target tissue lateral to one side of the urethra UR. If applicable, a temperature probe is then deployed from the probe tip to monitor the temperature of the vasoconstricted target tissue. Heating energy is then applied to the tissue, in this example by delivery of RF current by the probe 10, to cause resistive heating. RF energy is removed when either the target tissue temperature reaches the desired temperature or the maximum treatment time is reached. After removal of energy, the probe 10 and temperature probe are removed from the vagina V, reinserted into the vagina V and positioned on the contralateral side of the urethra UR. The treatment process is then repeated.

Figure 6A:
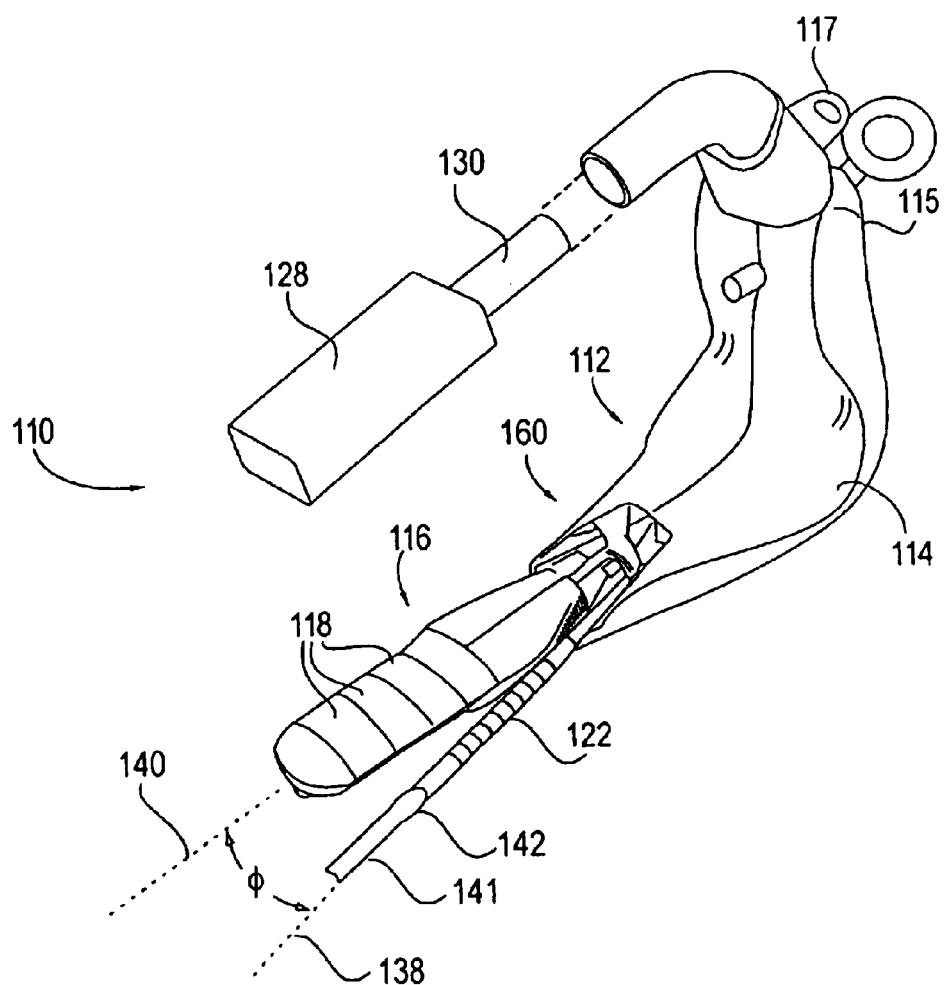
FIG. 6A is a perspective view of a tissue contraction probe and an attached guide shaft which may be used in conjunction with the methods of the present invention.

Referring to FIG. 6A, another embodiment of a tissue contraction probe 110 used to deliver RF energy is shown. The probe 110 includes an applicator or probe body 112 having a proximal portion 114 and a distal portion 116. Proximal portion 114 of the probe body 112 generally includes a handle 115 and a trigger or switch 117 for activating a delivery of electrical energy to the target tissue or for deploying a temperature probe into the target tissue to monitor the tissue temperature during treatment. Distal portion 116 includes a treatment surface 118 that has at least one electrode or other type of treatment assembly, such as an electrode on a needle, ultrasound transducer, microwave antenna, or needle for delivery of a therapeutic agent (not shown).

Figure 6B:
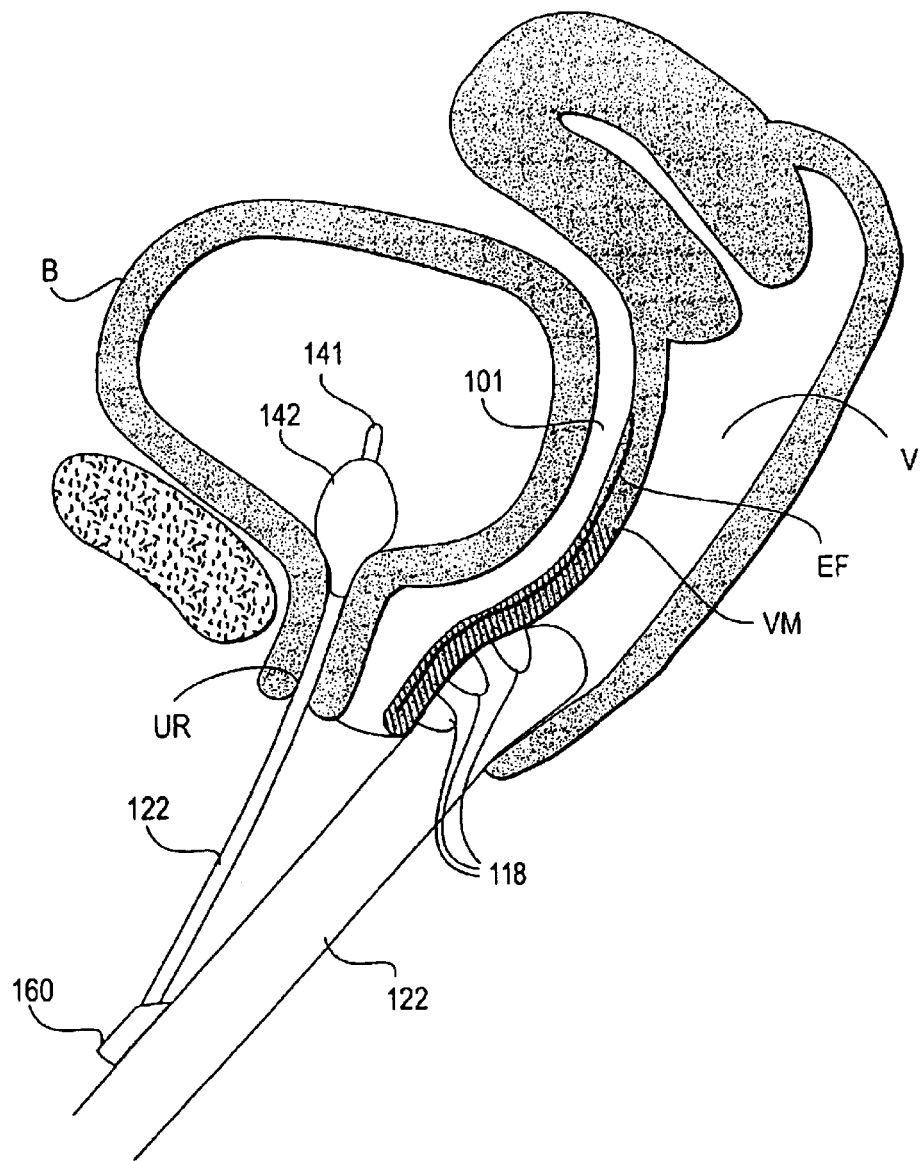
FIG. 6B illustrates the guide shaft and probe of FIG. 6A positioned within the urethra and vagina respectively to treat the target tissue

Also shown in FIG. 6A, a guide body or shaft 122 can be attached to the probe body 112 to assist in the proper positioning of the distal portion 116 of probe body 112 and treatment surface 118 with a target tissue. Generally, the probe body 12 is configured to be insertable in a first body orifice while guide shaft 122 is configured to be inserted into a second body orifice so as to accurately position the probe body 12 and electrodes 118 adjacent a target tissue in the first body orifice. By maintaining a substantially rigid connection between the probe body 12 and guide shaft 122 with a coupling assembly 160, guide 122 can properly position electrodes 118 so that they are offset laterally from a sensitive non-target tissue. For example, as illustrated in FIG. 6B, the guide shaft 122 may be positioned into a patent's urethra UR while the probe body 112 is inserted into the patient's vagina V. Here the urethral guide shaft 122 has a diameter and length so that an expansible member 142 disposed near a guide tip 141 is positionable and inflatable within the bladder B. Such positioning of the expansible member 142 holds the guide shaft 122 in position and therefore holds the rigidly attached probe body 112 in a relative position. Such configuration can prevent inadvertent delivery of electrical energy to the non-targeted tissue, such as the bladder or urethral tissue. Exemplary embodiments of the tissue contraction probe 110 and guide shaft 122 are further described in commonly assigned U.S. patent application Ser. No. 09/991,368 (Attorney Docket No. 017761-002600US) now U.S. Pat. No. 6,685,623, the complete disclosure of which is incorporated herein by reference.

Figure 7:
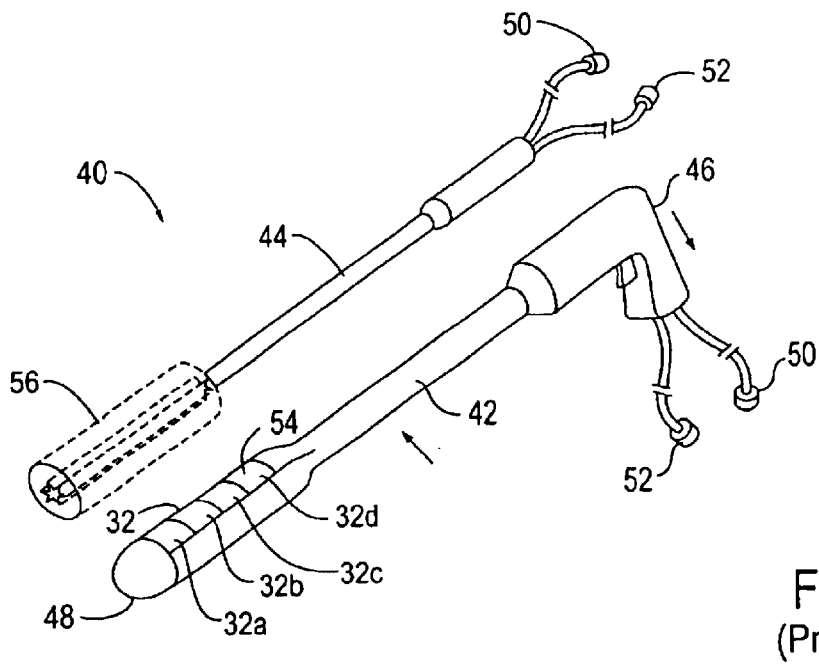
FIG. 7 is a perspective view of a bladder probe and a vaginal probe which may be used in conjunction with the methods of the present invention.

Although tissue contraction is typically achieved with the use of a single probe, a system of probes may be used in other embodiments to deliver energy. For example, as illustrated in FIG. 7, the system 40 includes a vaginal probe 42 and a bladder probe 44. The vaginal probe 42 has a proximal end 46 and a distal end 48. Electrode 32 (including segments 32a, 32b, 32c and 32d) is mounted near the distal end of the probe. Vaginal probe 42 will typically have a diameter of between about 2 and 4 cm, and will often have a shaft length of between about 6 and 12 cm. An electrical coupling 50 is couplable to an RF power supply, and optionally to an external control processor. Alternatively, a controller may be integrated into the probe itself. A fluid coupling 52 provides attachment to a cooling fluid system. Cooling fluid may be recycled through the probe so that more than one fluid couplers may be provided.

The segments of electrode 32 are quite close to each other, and preferably define a substantially flat electrode surface 54. The cooling fluid flows immediately below this surface, the surface material preferably being both thermally and electrically conductive. Ideally, surface 54 is as large as the tissue region to be treated, and a thermocouple or other temperature sensor may be mounted adjacent the surface for engaging the tissue surface and measuring the temperature of the engaged tissue.

Figure 8:
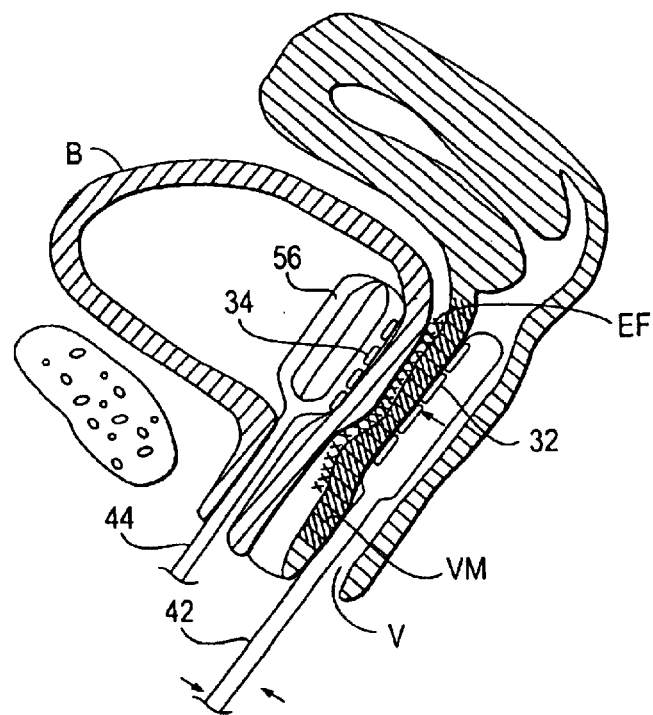
FIG. 8 illustrates the probes of FIG. 7 positioned with the bladder and vagina respectively to treat the target tissue.

Urethral probe 44 includes a balloon 56 supporting a deployable electrode surface. This allows the use of a larger electrode surface than could normally be inserted through the urethra, by expanding the balloon structure within the bladder as illustrated in FIG. 8. Alternatively, a narrower cylindrical electrode might be used which engages the surrounding urethra, the urethral electrode optionally being separated into more than one segment along the length and/or around the circumference of the probe shaft. Radiofrequency current will divert from such a tightly curved surface and heat the nearby tissue. The electrode can again be chilled to protect the urethral lining from thermal damage.

As illustrated in FIG. 8, the endopelvic fascia will preferably be disposed between the electrodes of the urethral probe 44 and vaginal probe 42. Balloon 56 of urethral probe 44 is here illustrated in its expanded configuration, thereby maximizing a surface area of electrode 34, and also minimizing its curvature. Preferably, cooled fluid recirculating through balloon 56 will cool electrode 34, so that cooled electrodes 32, 34 will selectively heat the endopelvic fascia EF without damaging the delicate vaginal mucosa VM or the bladder wall.

Urethral probe 44 and vaginal probe 42 may optionally be coupleable to each other to facilitate aligning the probes on either side of the target tissue, either mechanically or by some remote sensing system. For example, one of the probes may include an ultrasound transducer, thereby facilitating alignment of the electrode surfaces and identification of the target tissue. Alternatively, the proximal ends of the probes may attach together to align the electrodes and/or clamp the target tissue between the probes.

Although the above example focused on tissue contraction, similar methods may be used for tissue stiffening. However, regardless of the method of delivering energy for tissue contraction or tissue stiffening, the prior application of vasoconstrictive agents 200 reduces the possibility of undesirable heating and damage to intervening tissues. As mentioned, the vasoconstricting agents 200 cause the smooth muscle cells of arteries with the tissue to contract and decrease in size. This diminishes the flow volume and tissue contact area of the blood in the region being heated thus decreasing the effectiveness of blood flow as a heat sink. This allows the target tissue to be heated to the desired therapeutic effect with less power applied.

Figure 9:
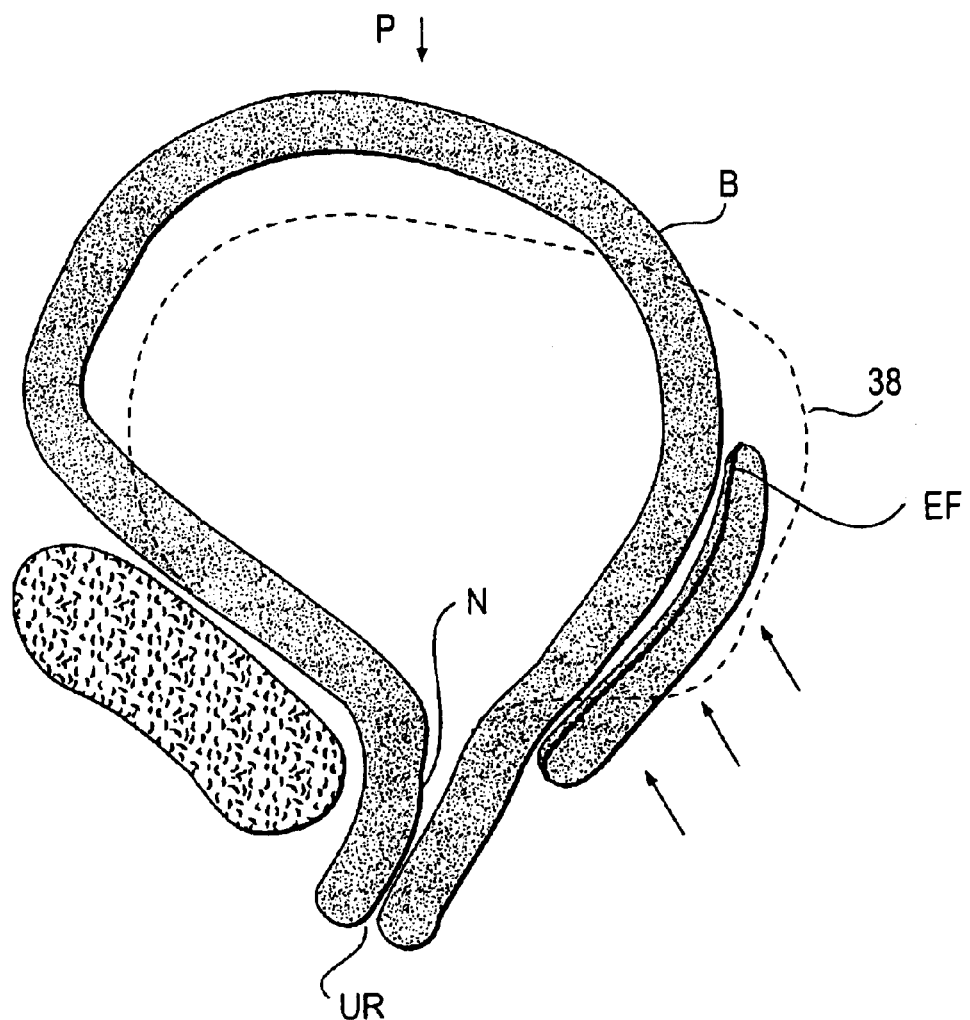
FIG. 9 illustrates the bladder of FIG. 1 after treatment wherein the bladder has been raised.

FIG. 9 illustrates positioning of the bladder B after treatment by the above described methods. As shown, the bladder B can be elevated from its lowered position (shown by dashed outline 38). A pressure pulse P is resisted in part by endopelvic fascia EF, which supports the lower portion of the bladder and helps maintain the bladder neck N in a closed configuration. In fact, fine-tuning of the support provided by the endopelvic fascia is possible through selective contraction of the anterior portion of the endopelvic fascia to close the bladder neck and raise bladder B upward. Alternatively, lateral repositioning of bladder B to a more forward position may be effected by selectively contracting the dorsal portion of endopelvic fascia EF. Hence, the treatment may be tailored to the particular weakening exhibited by a patient's pelvic support structures.

Figure 10:
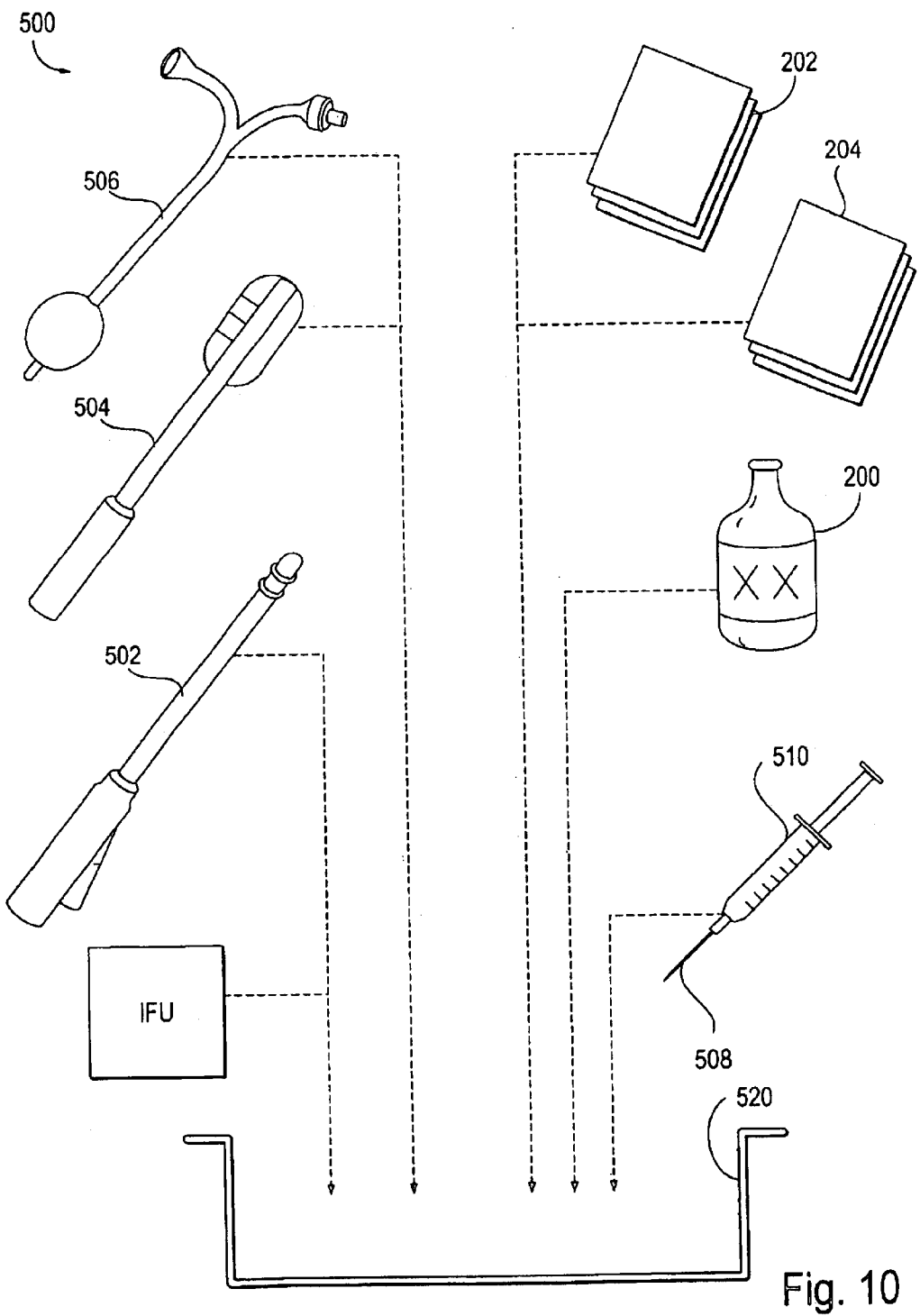
FIG. 10 illustrates a kit constructed in accordance with the principles of the present invention.

The methods and systems of the present invention may be provided in one or more kits for such use. Referring now to FIG. 10, kits 500 according to the present invention comprise at least a vasoconstrictive agent 200 and instructions for use IFU. Optionally, the kits may further include one or more of any of the other system components described above, such as a probe 502, an additional probe 504 for use alone or in conjunction with probe 502, a guide 506, a carrier 202, additional material 204 and a needle 508 and syringe 510, to name a few. The instructions for use IFU will set forth any of the methods as described above, and all kit components will usually be packaged together in a pouch 520 or other conventional medical device packaging. Usually, those kit components, such as a probe 502, which will be used in performing the procedure on the patient will be sterilized and maintained within the kit. Optionally, separate pouches, bags, trays or other packaging may be provided within a larger package, where the smaller packs may be opened separately to separately maintain the components in a sterile fashion.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method of treating a target tissue of a patient body comprising:
   introducing a vasoconstrictive agent supported by a carrier to the target tissue to form a vasoconstricted target tissue, wherein introducing the vasoconstrictive agent comprises applying the agent to a surface of the target tissue, by holding the carrier against the target tissue;
   positioning a probe having a heat-applying element so that the element is aligned with the vasoconstricted target tissue; and
   energizing the probe to heat a portion of the vasoconstricted target tissue.

2. A method as in claim 1, wherein the vasoconstrictive agent comprises epinephrme.

3. A method as in claim 1, wherein the vasoconstrictive agent is ionized and further comprising electrically stimulating the agent and/or target tissue to assist absorption of the agent.

4. A method as in claim 1, further comprising ultrasonically stimulating the agent and/or target tissue to assist absorption of the agent.

5. A method as in claim 1, wherein introducing the vasoconstrictive agent further comprises injecting the agent into the target tissue.

6. A method as in claim 1, wherein energizing the probe comprises providing radiofrequency energy, microwave energy, light or laser energy, electrical resistance heating, heated fluids, or ultrasound energy.

7. A method as in claim 1, wherein the heat applying elements comprise first and second electrodes, and wherein energizing the probe comprises applying an electrical potential across the first and second electrodes to heat the portion of the vasoconstricted target tissue.

8. A method as in claim 1, wherein the target tissue comprises a pelvic support tissue and wherein energizing the probe to heat the portion of the vasoconstricted target tissue reduces urinary incontinence.

9. A method as in claim 1, wherein the heat applying elements comprise a plurality of electrode segments and the probe further comprises a cooling fluid system which cools the electrode segments, said method further comprising cooling a portion of the vasoconstricted target tissue adjacent the probe with the cooled electrode segments.

10. A method as in claim 1, positioning another probe having at least one heat-applying element so that the vasoconstricted target tissue is disposed between the heat-applying elements of the probe and the another probe.

11. A method as in claim 10, wherein the target tissue comprises the endopelvic fascia, the probe comprises a vaginal probe and positioning the probe comprises inserting the vaginal probe into a vagina, and the another probe comprises a urethral probe and positioning the another probe comprises inserting the urethral probe into a urethra.

12. A system for treating a target tissue of a patient body comprising:
   a vasoconstrictive agent comprising epinephrine and having a form of a liquid or paste, the agent absorbable by at least a portion of the target tissue to form a vasoconstricted target tissue and the agent having a concentration in the range of 1 mg agent per 25 ml solution to 1 mg agent per 200 ml solution;
   a carrier comprising gauze upon or within which the vasoconstrictive agent is disposed; and
   a probe having a proximal end, a distal end and at least one heat-applying element near its distal end positionable near the vasoconstricted target tissue so that energizing the probe heats a portion of the vasoconstricted target tissue.

13. A system as in claim 12, wherein the agent is ionizable.

14. A system as in claim 12, wherein heat-applying elements deliver radiofrequency energy, microwave energy, light or laser energy, electrical resistance heating, heated fluids, or ultrasound energy.

15. A system as in claim 14, wherein the heat-applying elements comprise electrodes.

16. A system as in claim 15, wherein the electrodes deliver a maximum power of 50 watts.

17. A system as in claim 15, wherein the heat-applying elements comprise a plurality of electrode segments and the probe further comprises a cooling fluid system which cools the electrode segments.

18. A system as in claim 12, further comprising another probe having a proximal end, a distal end and at least one heat-applying element near its distal end positionable near the vasoconstricted target tissue so that the vasoconstricted target tissue is disposed between the heat-applying elements of the probe and the another probe.

19. A system as in claim 18, wherein the target tissue comprises the endopelvic fascia, the probe comprises a vaginal probe positionable within a vagina and the another probe comprises a urethral probe positionable within a urethra.

20. A system as in claim 12, further comprising a guide which is engageable with the probe to maintain the probe at a position relative to the guide.

21. A method to treat urinary stress incontinence, the method comprising:
   introducing a vasoconstrictive agent to a pelvic support tissue which supports the bladder or urethra to form a vasoconstricted tissue;
   aligning a probe with the vasoconstricted tissue;
   energizing the probe to heat a portion of the vasoconstricted tissue so that the tissue is altered reducing incontinence.

22. A method as in claim 21, wherein the vasoconstrictive agent comprises epinephrmne.

23. A method as in claim 21, wherein introducing the vasoconstrictive agent comprises applying the agent to the vaginal mucosa.

24. A method as in claim 23, wherein aligning the probe comprises inserting the probe within a vagina.

25. A method as in claim 24, wherein the probe has a proximal end, a distal end, and at least one heat-applying element near its distal end, said method further comprising aligning the probe so that its heat-applying element is aligned with the vaginal mucosa.

26. A method as in claim 23, wherein energizing the probe heats the endopelvic fascia.

27. A method as in claim 21, wherein the probe comprises heat applying elements and wherein energizing the probe comprises providing radiofrequency energy, microwave energy, light or laser energy, electrical resistance heating, heated fluids, or ultrasound energy with the use of the heat-applying elements.

28. A method as in claim 27, wherein the heat applying elements comprise a plurality of electrode segments and the probe further comprises a cooling fluid system which cools the electrode segments, said method further comprising cooling the vasoconstricted tissue adjacent the probe with the cooled electrode segments.

29. A method as in claim 21, further comprising positioning another probe having heat-applying elements near the vasoconstricted tissue so that the portion of the vasoconstricted tissue is disposed between the heat applying elements of the probe and the another probe.

30. A method as in claim 29, further comprising energizing the another probe while energizing the probe to heat the portion of the vasoconstricted tissue disposed between the heat applying elements of the probe and the another probe.

31. A method as in claim 29, wherein the probe comprises a vaginal probe and aligning the probe comprises inserting the vaginal probe into a vagina, and the another probe comprises a urethral probe and aligning the another probe comprises inserting the urethral probe into a urethra.

32. A method as in claim 21, further comprising introducing a guide to a urethra.

33. A method as in claim 32, further comprising attaching the probe to the guide to maintain the probe at a position relative to the guide.

34. A kit comprising:
   a vasoconstrictive agent;
   a carrier which is capable of carrying the vasoconstrictive agent;
   a guide; and
   instructions for use setting forth a method comprising the steps of
      introducing the vasoconstrictive agent to a target tissue so that the agent is absorbed to form a vasoconstricted target tissue; and
      energizing a probe to heat a portion of the vasoconstricted target tissue.

35. A kit as in claim 34, further comprising the probe.

36. A kit as in claim 34, wherein the vasoconstrictive agent comprises epinephrine.

37. A kit as in claim 34, further comprising a syringe within which the vasoconstrictive agent is loadable.

38. A method of treating a target tissue of a patient body comprising:
   introducing a vasoconstrictive agent to the target tissue, wherein the target tissue comprises a pelvic support tissue, to form a vasoconstricted target tissue;
   positioning a probe having a heat-applying element so that the element is aligned with the vasoconstricted target tissue; and energizing the probe to heat a portion of the vasoconstricted target tissue which reduces urinary incontinence.

39. A method as in claim 38, wherein the vasoconstrictive agent comprises epinephrine.

40. A method as in claim 38, wherein introducing the vasoconstrictive agent comprises applying the agent to a surface of the target tissue.

41. A method as in claim 40, wherein the agent is supported by a carrier and applying the agent to the surface comprises holding the carrier against the target tissue.

42. A method as in claim 40, wherein the vasoconstrictive agent is ionized and further comprising electrically stimulating the agent and/or target tissue to assist absorption of the agent.

43. A method as in claim 46, further comprising ultrasonically stimulating the agent and/or target tissue to assist absorption of the agent.

44. A method as in claim 38, wherein introducing the vasoconstrictive agent comprises injecting the agent into the target tissue.

45. A method as in claim 38, wherein energizing the probe comprises providing radiofrequency energy, microwave energy, light or laser energy, electrical resistance heating, heated fluids, or ultrasound energy.

46. A method as in claim 38, wherein the heat applying elements comprise first and second electrodes, and wherein energizing the probe comprises applying an electrical potential across the first and second electrodes to heat the portion of the vasoconstricted target tissue.

47. A method as in claim 38, wherein the heat applying elements comprise a plurality of electrode segments and the probe further comprises a cooling fluid system which cools the electrode segments, said method further comprising cooling a portion of the vasoconstricted target tissue adjacent the probe with the cooled electrode segments.

48. A method as in claim 38, positioning another probe having at least one heat-applying element so that the vasoconstricted target tissue is disposed between the heat-applying elements of the probe and the another probe.

49. A method as in claim 48, where in the target tissue comprises the endopelvic fascia, the probe comprises a vaginal probe and positioning the probe comprises inserting the vaginal probe into a vagina, and the another probe comprises a urethral probe and positioning the another probe comprises inserting the urethral probe into a urethra.

50. A method of treating a target tissue of a patient body comprising:
    introducing a vasoconstrictive agent to the target tissue to form a vasoconstricted target tissue, wherein introducing the vasoconstrictive agent comprises injecting the agent into the target tissue;
    positioning a probe having a heat-applying element so that the element is aligned with the vasoconstricted target tissue, wherein the heat applying elements comprise a plurality of electrode segments and the probe further comprises a cooling fluid system which cools the electrode segments;
    energizing the probe to heat a portion of the vasoconstricted target tissue; and
    cooling a portion of the vasoconstricted target tissue adjacent the probe with the cooled electrode segments.

51. A method as in claim 50, wherein the vasoconstrictive agent comprises epinephrine.

52. A method as in claim 50, wherein the vasoconstrictive agent is ionized and further comprising electrically stimulating the agent and/or target tissue to assist absorption of the agent.

53. A method as in claim 50, wherein the heat applying elements comprise first and second electrodes, and wherein energizing the probe comprises applying an electrical potential across the first and second electrodes to heat the portion of the vasoconstricted target tissue.

54. A method as in claim 50, wherein the target tissue comprises a pelvic support tissue and wherein energizing the probe to heat the portion of the vasoconstricted target tissue reduces urinary incontinence.

55. A method of treating a target tissue of a patient body comprising:
    introducing a vasoconstrictive agent to the target tissue to form a vasoconstricted target tissue;
    positioning a probe having a heat-applying element so that the element is aligned with the vasoconstricted target tissue;
    energizing the probe to heat a portion of the vasoconstricted target tissue; and
    positioning another probe having at least one heat-applying element so that the vasoconstricted target tissue is disposed between the heat-applying elements of the probe and the another probe.

56. A system for treating a target tissue of a patient body comprising:
    a vasoconstrictive agent comprising epinephrine, wherein the agent is absorbable by at least a portion of the target tissue to form a vasoconstricted target tissue and the agent is ionizable, wherein the vasoconstrictive agent has a form of a liciuid or paste;
    a carrier upon or within which the vasoconstrictive agent is disposed, wherein the carrier comprises gauze; and
    a probe having a proximal end, a distal end and at least one heat-applying element near its distal end positionable near the vasoconstricted target tissue so that energizing the probe heats a portion of the vasoconstricted target tissue.

57. A system as in claim 56, wherein the agent has a concentration in the range of 1 mg agent per 25 ml solution to 1 mg agent per 200 ml solution.

58. A system as in claim 56, wherein heat-applying elements deliver radiofrequency energy, microwave energy, light or laser energy, electrical resistance heating, heated fluids, or ultrasound energy.

59. A system as in claim 58, wherein the heat-applying elements comprise electrodes.

60. A system as in claim 59, wherein the electrodes deliver a maximum power of 50 watts.

61. A system as in claim 59, wherein the heat-applying elements comprise a plurality of electrode segments and the probe further comprises cooling fluid system which cools the electrode segments.

62. A system for treating a target tissue of a patient body comprising:
    a vasoconstrictive agent absorbable by at least a portion of the target tissue to form a vasoconstricted target tissue, wherein the vasoconstrictive agent has a form of a liquid or paste;
    a carrier upon or within which the vasoconstrictive agent is disposed, wherein the carrier comprises gauze; and
    a probe having a proximal end, a distal end and at least one heat-applying element near its distal end positionable near the vasoconstricted target tissue so that energizing the probe heats a portion of the vasoconstricted target tissue.

63. A system as in claim 62, wherein the vasoconstrictive agent is comprises epinephrine.

64. A system as in claim 63, wherein the agent has a concentration in the range of 1 mg agent per 25 ml solution to 1 mg agent per 200 ml solution.

65. A system as in claim 62, wherein the agent is ionizable.

66. A system as in claim 62, wherein heat-applying elements deliver radiofrequency energy, microwave energy, light or laser energy, electrical resistance heating, heated fluids, or ultrasound energy.

67. A system as in claim 66, wherein the heat-applying elements comprise electrodes.

68. A system as in claim 67, wherein the electrodes deliver a maximum power of 50 watts.

69. A system as in claim 67, wherein the heat-applying elements comprise a plurality of electrode segments and the probe further comprises a cooling fluid system which cools the electrode segments.

70. A system as in claim 62, further comprising a guide which is engageable with the probe to maintain the probe at a position relative to the guide.

71. A system for treating a target tissue of a patient body comprising:
    a vasoconstrictive agent absorbable by at least a portion of the target tissue to form a vasoconstricted target tissue; and
    a probe having a proximal end, a distal end and at least one heat-applying element comprising a plurality of electrode segments near its distal end positionable near the vasoconstricted target tissue so that energizing the probe heats a portion of the vasoconstricted target tissue, the at least one heat-applying element delivering radiofrequency energy, microwave energy, light or laser energy, electrical resistance heating, heated fluids or ultrasound energy, and the probe further comprises a cooling fluid system which cools the electrode segments.

72. A system as in claim 71, wherein the vasoconstrictive agent is comprises epinephrine.

73. A system as in claim 71, further comprising a carrier upon or within which the vasoconstrictive agent is disposed.

74. A system as in claim 71, further comprising a needle and a syringe within which the vasoconstrictive agent is loaded.

75. A system for treating a target tissue of a patient body comprising:
    a vasoconstrictive agent absorbable by at least a portion of the target tissue to form a vasoconstricted target tissue;
    a probe having a proximal end, a distal end and at least one heat-applying element near its distal end positionable near the vasoconstricted target tissue so that energizing the probe heats a portion of the vasoconstricted target tissue;
    another probe having a proximal end, a distal end and at least one heat-applying element near its distal end positionable near the vasoconstricted target tissue so that the vasoconstricted target tissue is disposed between the heat-applying elements of the probe and the another probe.

76. A system for treating a target tissue of a patient body comprising:
    a vasoconstrictive agent absorbable by at least a portion of the target tissue to form a vasoconstricted target tissue;
    a probe having a proximal end, a distal end and at least one heat-applying element near its distal end positionable near the vasoconstricted target tissue so that energizing the probe heats a portion of the vasoconstricted target tissue; and
    a guide which is engageable with the probe to maintain the probe at a position relative to the guide.

77. A system as in claim 76, wherein the vasoconstrictive agent is comprises epinephrine.

78. A system as in claim 76, further comprising a carrier upon or within which the vasoconstrictive agent is disposed.

79. A system as in claim 76, further comprising a needle and a syringe within which the vasoconstrictive agent is loaded.

80. A method of treating a target tissue of a patient body comprising:
    introducing a vasoconstrictive agent which is ionized to the target tissue to form a vasoconstricted target tissue, wherein introducing the vasoconstrictive agent comprises applying the agent to a surface of the target tissue;
    positioning a probe having a heat-applying element so that the element is aligned with the vasoconstricted target tissue;
    energizing the probe to heat a portion of the vasoconstricted target tissue; and
    electrically stimulating the agent and/or target tissue to assist absorption of the agent.

81. A method as in claim 80, wherein the vasoconstrictive agent comprises epinephrine.

82. A method as in claim 80, wherein the agent is supported by a carrier and applying the agent to the surface comprises holding the carrier against the target tissue.

83. A method as in claim 80, further comprising ultrasonically stimulating the agent and/or target tissue to assist absorption of the agent.

84. A method as in claim 80, wherein introducing the vasoconstrictive agent further comprises injecting the agent into the target tissue.

85. A method as in claim 80, wherein energizing the probe comprises providing radiofrequency energy, microwave energy, light or laser energy, electrical resistance heating, heated fluids, or ultrasound energy.

86. A method as in claim 80, wherein the heat applying elements comprise first and second electrodes, and wherein energizing the probe comprises applying an electrical potential across the first and second electrodes to heat the portion of the vasoconstricted target tissue.

87. A method as in claim 80, wherein the target tissue comprises a pelvic support tissue and wherein energizing the probe to heat the portion of the vasoconstricted target tissue reduces urinary incontinence.

88. A method as in claim 80, wherein the heat applying elements comprise a plurality of electrode segments and the probe further comprises a cooling fluid system which cools the electrode segments, said method further comprising cooling a portion of the vasoconstricted target tissue adjacent the probe with the cooled electrode segments.

89. A method as in claim 80, positioning another probe having at least one heat-applying element so that the vasoconstricted target tissue is disposed between the heat-applying elements of the probe and the another probe.

90. A method as in claim 89, wherein the target tissue comprises the endopelvic fascia, the probe comprises a vaginal probe and positioning the probe comprises inserting the vaginal probe into a vagina, and the another probe comprises a urethral probe and positioning the another probe comprises inserting the urethral probe into a urethra.

91. A method of treating a target tissue of a patient body comprising:
    introducing a vasoconstrictive agent to the target tissue to form a vasoconstricted target tissue, wherein introducing the vasoconstrictive agent comprises applying the agent to a surface of the target tissue;

positioning a probe having a heat-applying element so that the element is aligned with the vasoconstricted target tissue;

energizing the probe to heat a portion of the vasoconstricted target tissue; and ultrasonically stimulating the agent and/or target tissue to assist absorption of the agent.

92. A method as in claim 91, wherein the vasoconstrictive agent comprises epinephrine.

93. A method as in claim 91, wherein the agent is supported by a carrier and applying the agent to the surface comprises holding the carrier against the target tissue.

94. A method as in claim 91, wherein the vasoconstrictive agent is ionized and further comprising electrically stimulating the agent and/or target tissue to assist absorption of the agent.

95. A method as in claim 91, wherein introducing the vasoconstrictive agent further comprises injecting the agent into the target tissue.

96. A method as in claim 91, wherein energizing the probe comprises providing radiofrequency energy, microwave energy, light or laser energy, electrical resistance heating, heated fluids, or ultrasound energy.

97. A method as in claim 91, wherein the heat applying elements comprise first and second electrodes, and wherein energizing the probe comprises applying an electrical potential across the first and second electrodes to heat the portion of the vasoconstricted target tissue.

98. A method as in claim 91, wherein the target tissue comprises a pelvic support tissue and wherein energizing the probe to heat the portion of the vasoconstricted target tissue reduces urinary incontinence.

99. A method as in claim 91, wherein the heat applying elements comprise a plurality of electrode segments and the probe further comprises a cooling fluid system which cools the electrode segments, said method further comprising cooling a portion of the vasoconstricted target tissue adjacent the probe with the cooled electrode segments.

100. A method as in claim 91, positioning another probe having at least one heat-applying element so that the vasoconstricted target tissue is disposed between the heat-applying elements of the probe and the another probe.

101. A method as in claim 100, wherein the target tissue comprises the endopelvic fascia, the probe comprises a vaginal probe and positioning the probe comprises inserting the vaginal probe into a vagina, and the another probe comprises a urethral probe and positioning the another probe comprises inserting the urethral probe into a urethra.

102. A method of treating a target tissue of a patient body comprising:

introducing a vasoconstrictive agent to the target tissue to form a vasoconstricted target tissue, wherein introducing the vasoconstrictive agent comprises applying the agent to a surface of the target tissue and injecting the agent into the target tissue;

positioning a probe having a heat-applying element so that the element is aligned with the vasoconstricted target tissue; and energizing the probe to heat a portion of the vasoconstricted target tissue.

103. A method as in claim 102, wherein the vasoconstrictive agent comprises epinephrmne.

104. A method as in claim 102, applying the agent to the surface comprises holding a carrier supporting the agent against the target tissue.

105. A method as in claim 102, wherein the vasoconstrictive agent is ionized and further comprising electrically stimulating the agent and/or target tissue to assist absorption of the agent.

106. A method as in claim 102, further comprising ultrasonically stimulating the agent and/or target tissue to assist absorption of the agent.

107. A method as in claim 102, wherein energizing the probe comprises providing radiofrequency energy, microwave energy, light or laser energy, electrical resistance heating, heated fluids, or ultrasound energy.

108. A method as in claim 102, wherein the heat applying elements comprise first and second electrodes, and wherein energizing the probe comprises applying an electrical potential across the first and second electrodes to heat the portion of the vasoconstricted target tissue.

109. A method as in claim 102, wherein the target tissue comprises a pelvic support tissue and wherein energizing the probe to heat the portion of the vasoconstricted target tissue reduces urinary incontinence.

110. A method as in claim 102, wherein the heat applying elements comprise a plurality of electrode segments and the probe further comprises a cooling fluid system which cools the electrode segments, said method further comprising cooling a portion of the vasoconstricted target tissue adjacent the probe with the cooled electrode segments.

111. A method as in claim 102, positioning another probe having at least one heat-applying element so that the vasoconstricted target tissue is disposed between the heat-applying elements of the probe and the another probe.

112. A method as in claim 111, wherein the target tissue comprises the endopelvic fascia, the probe comprises a vaginal probe and positioning the probe comprises inserting the vaginal probe into a vagina, and the another probe comprises a urethral probe and positioning the another probe comprises inserting the urethral probe into a urethra.

113. A method of treating a target tissue of a patient body comprising:

introducing a vasoconstrictive agent to the target tissue to form a vasoconstricted target tissue wherein the target tissue comprises a pelvic support tissue, wherein introducing the vasoconstrictive agent comprises applying the agent to a surface of the target tissue;

positioning a probe having a heat-applying element so that the element is aligned with the vasoconstricted target tissue; and energizing the probe to heat a portion of the vasoconstricted target tissue which reduces urinary incontinence.

114. A method as in claim 113, wherein the vasoconstrictive agent comprises epinephrine.

115. A method as in claim 113, wherein the agent is supported by a carrier and applying the agent to the surface comprises holding the carrier against the target tissue.

116. A method as in claim 113, wherein the vasoconstrictive agent is ionized and further comprising electrically stimulating the agent and/or target tissue to assist absorption of the agent.

117. A method as in claim 113, further comprising ultrasonically stimulating the agent and/or target tissue to assist absorption of the agent.

118. A method as in claim 113, wherein introducing the vasoconstrictive agent further comprises injecting the agent into the target tissue.

119. A method as in claim 113, wherein energizing the probe comprises providing radiofrequency energy, microwave energy, light or laser energy, electrical resistance heating, heated fluids, or ultrasound energy.

120. A method as in claim 113, wherein the heat applying elements comprise first and second electrodes, and wherein energizing the probe comprises applying an electrical potential across the first and second electrodes to heat the portion of the vasoconstricted target tissue.

121. A method as in claim 113, wherein the heat applying elements comprise a plurality of electrode segments and the probe further comprises a cooling fluid system which cools the electrode segments, said method further comprising cooling a portion of the vasoconstricted target tissue adjacent the probe with the cooled electrode segments.

122. A method as in claim 113, positioning another probe having at least one heat-applying element so that the vasoconstricted target tissue is disposed between the heat-applying elements of the probe and the another probe.

123. A method as in claim 122, wherein the target tissue comprises the endopelvic fascia, the probe comprises a vaginal probe and positioning the probe comprises inserting the vaginal probe into a vagina, and the another probe comprises a urethral probe and positioning the another probe comprises inserting the urethral probe into a urethra.

124. A method of treating a target tissue of a patient body comprising:
    introducing a vasoconstrictive agent to the target tissue to form a vasoconstricted target tissue, wherein introducing the vasoconstrictive agent comprises applying the agent to a surface of the target tissue;
    positioning a probe having a heat-applying element so that the element is aligned with the vasoconstricted target tissue;
    positioning another probe having at least one heat-applying element so that the vasoconstricted target tissue is disposed between the heat-applying elements of the probe and the another probe; and
    energizing the probe to heat a portion of the vasoconstricted target tissue.

125. A method as in claim 124, wherein the vasoconstrictive agent comprises epinephrine.

126. A method as in claim 124, wherein the agent is supported by a carrier and applying the agent to the surface comprises holding the carrier against the target tissue.

127. A method as in claim 124, wherein the vasoconstrictive agent is ionized and further comprising electrically stimulating the agent and/or target tissue to assist absorption of the agent.

128. A method as in claim 124, further comprising ultrasonically stimulating the agent and/or target tissue to assist absorption of the agent.

129. A method as in claim 124, wherein introducing the vasoconstrictive agent further comprises injecting the agent into the target tissue.

130. A method as in claim 124, wherein energizing the probe comprises providing radiofrequency energy, microwave energy, light or laser energy, electrical resistance heating, heated fluids, or ultrasound energy.

131. A method as in claim 124, wherein the heat applying elements comprise first and second electrodes, and wherein energizing the probe comprises applying an electrical potential across the first and second electrodes to heat the portion of the vasoconstricted target tissue.

132. A method as in claim 124, wherein the target tissue comprises a pelvic support tissue and wherein energizing the probe to heat the portion of the vasoconstricted target tissue reduces urinary incontinence.

133. A method as in claim 124, wherein the heat applying elements comprise a plurality of electrode segments and the probe further comprises a cooling fluid system which cools the electrode segments, said method further comprising cooling a portion of the vasoconstricted target tissue adjacent the probe with the cooled electrode segments.

134. A method as in claim 124, wherein the target tissue comprises the endopelvic fascia, the probe comprises a vaginal probe and positioning the probe comprises inserting the vaginal probe into a vagina, and the another probe comprises a urethral probe and positioning the another probe comprises inserting the urethral probe into a urethra.

135. A system for treating a target tissue of a patient body comprising:
    a vasoconstrictive agent comprising epinephrine, the agent absorbable by at least a portion of the target tissue to form a vasoconstricted target tissue, wherein the target tissue comprises the endopelvic fascia, and the agent has a concentration in the range of 1 mg agent per 25 ml solution to 1 mg agent per 200 ml solution;
    a probe having a proximal end, a distal end and at least one heat-applying element near its distal end positionable near the vasoconstricted target tissue so that energizing the probe heats a portion of the vasoconstricted target tissue, wherein the probe comprises a vaginal probe positionable within a vagina; and
    another probe having a proximal end, a distal end and at least one heat-applying element near its distal end positionable near the vasoconstricted target tissue so that the vasoconstricted target tissue is disposed between the heat-applying elements of the probe and the another probe, wherein the another probe comprises a urethral probe positionable within a urethra.

136. A system as in claim 135, wherein the agent is ionizable.

137. A system as in claim 135, further comprising a carrier upon or within which the vasoconstrictive agent is disposed.

138. A system as in claim 137, wherein the vasoconstrictive agent has a form of a liquid or paste and the carrier comprises gauze.

139. A system as in claim 135, further comprising a needle and a syringe within which the vasoconstrictive agent is loaded.

140. A system as in claim 135, wherein heat-applying elements deliver radiofrequency energy, microwave energy, light or laser energy, electrical resistance heating, heated fluids, or ultrasound energy.

141. A system as in claim 140, wherein the heat-applying elements comprise electrodes.

142. A system as in claim 141, wherein the electrodes deliver a maximum power of 50 watts.

143. A system as in claim 141, wherein the heat-applying elements comprise a plurality of electrode segments and the probe further comprises a cooling fluid system which cools the electrode segments.

144. A system as in claim 135, further comprising a guide which is engageable with the probe to maintain the probe at a position relative to the guide.

145. A system for treating a target tissue of a patient body comprising:
    a vasoconstrictive agent comprising epinephrine, the agent absorbable by at least a portion of the target tissue to form a vasoconstricted target tissue and the agent having a concentration in the range of 1 mg agent per 25 ml solution to 1 mg agent per 200 ml solution;
    a probe having a proximal end, a distal end and at least one heat-applying element near its distal end positionable near the vasoconstricted target tissue so that energizing the probe heats a portion of the vasoconstricted target tissue; and a guide which is engageable with the probe to maintain the probe at a position relative to the guide.

146. A system as in claim 145, wherein the agent is ionizable.

147. A system as in claim 145, further comprising a carrier upon or within which the vasoconstrictive agent is disposed.

148. A system as in claim 147, wherein the vasoconstrictive agent has a form of a liquid or paste and the carrier comprises gauze.

149. A system as in claim 145, further comprising a needle and a syringe within which the vasoconstrictive agent is loaded.

150. A system as in claim 145, wherein heat-applying elements deliver radiofrequency energy, microwave energy, light or laser energy, electrical resistance heating, heated fluids, or ultrasound energy.

151. A system as in claim 150, wherein the heat-applying elements comprise electrodes.

152. A system as in claim 151, wherein the electrodes deliver a maximum power of 50 watts.

153. A system as in claim 151, wherein the heat-applying elements comprise a plurality of electrode segments and the probe further comprises a cooling fluid system which cools the electrode segments.

154. A system as in claim 145, further comprising another probe having a proximal end, a distal end and at least one heat-applying element near its distal end positionable near the vasoconstricted target tissue so that the vasoconstricted target tissue is disposed between the heat-applying elements of the probe and the another probe.

155. A system as in claim 154, wherein the target tissue comprises the endopelvic fascia, the probe comprises a vaginal probe positionable within a vagina and the another probe comprises a urethral probe positionable within a urethra.

156. A method of treating a target tissue of a patient body comprising:

introducing a vasoconstrictive agent to the target tissue to form a vasoconstricted target tissue, wherein the target tissue comprises a pelvic support tissue;

positioning a probe having a heat-applying element so that the element is aligned with the vasoconstricted target tissue, wherein the heat applying elements comprise a plurality of electrode segments and the probe further comprises a cooling fluid system which cools the electrode segments;

energizing the probe to heat a portion of the vasoconstricted target tissue which reduces urinary incontinence; and cooling a portion of the vasoconstricted target tissue adjacent the probe with the cooled electrode segments.

157. A system for treating a target tissue of a patient body comprising:

a vasoconstrictive agent absorbable by at least a portion of the target tissue to form a vasoconstricted target tissue;

a carrier upon or within which the vasoconstrictive agent is disposed;

a probe having a proximal end, a distal end and at least one heat-applying element near its distal end positionable near the vasoconstricted target tissue so that energizing the probe heats a portion of the vasoconstricted target tissue; and a guide which is engageable with the probe to maintain the probe at a position relative to the guide.

* * * * *